(12) United States Patent
Hurson (10) Patent No.: US 8,758,012 B2
(45) Date of Patent: Jun. 24, 2014

(54) COMPACT DENTAL IMPLANT

(75) Inventor: Steven M. Hurson, Yorba Linda, CA (US)

(73) Assignee: Nobel Biocare Services AG, Zurich-Flughafen (CH)

( * ) Notice: Subject to any disclaimer, the term of this patent is extended or adjusted under 35 U.S.C. 154(b) by 1180 days.

(21) Appl. No.: 12/172,881

(22) Filed: Jul. 14, 2008

(65) Prior Publication Data

US 2010/0009316 A1    Jan. 14, 2010

(51) Int. Cl.
*A61C 8/00*    (2006.01)

(52) U.S. Cl.
USPC .......................................... 433/173

(58) Field of Classification Search
USPC ........... 433/172–176, 201.1, 202.1, 215, 220, 433/221
See application file for complete search history.

(56) References Cited

U.S. PATENT DOCUMENTS

| | | | |
|---|---|---|---|
| 4,468,200 A | 8/1984 | Munch | |
| 4,738,623 A | 4/1988 | Driskell | |
| 4,863,383 A | 9/1989 | Grafelmann | |
| 5,000,686 A | 3/1991 | Lazzara et al. | |
| 5,044,853 A * | 9/1991 | Dicke | 411/311 |
| 5,226,766 A | 7/1993 | Lasner | |
| 5,259,398 A | 11/1993 | Vrespa | |
| 5,281,140 A | 1/1994 | Niznick | |
| 5,403,136 A | 4/1995 | Mathys | |
| 5,435,723 A * | 7/1995 | O'Brien | 433/174 |
| 5,601,429 A | 2/1997 | Blacklock | |
| 5,639,237 A * | 6/1997 | Fontenot | 433/173 |
| 5,702,346 A * | 12/1997 | Lazzara et al. | 433/173 |
| 5,810,589 A | 9/1998 | Michnick et al. | |
| 5,816,812 A * | 10/1998 | Kownacki et al. | 433/174 |
| 5,897,319 A | 4/1999 | Wagner et al. | |
| 5,967,783 A | 10/1999 | Ura | |
| 6,227,857 B1 | 5/2001 | Morgan et al. | |
| 6,402,515 B1 | 6/2002 | Palti et al. | |
| 6,547,564 B1 * | 4/2003 | Hansson | 433/174 |
| 6,585,740 B2 * | 7/2003 | Schlapfer et al. | 606/308 |
| 7,597,557 B2 | 10/2009 | Fromovich et al. | |
| 2004/0006346 A1 | 1/2004 | Holmen et al. | |

(Continued)

FOREIGN PATENT DOCUMENTS

| | | |
|---|---|---|
| EP | 0 696 445 | 2/1996 |
| EP | 1 598 028 | 11/2005 |

(Continued)

OTHER PUBLICATIONS

Machine translation of FR 2610512.*
Translation of FR2610512 retreived on Aug. 10, 2010.*
Niznick, Gerald A., DMD, MSD. "Proactive Nobel Active New Presentation," Implant Direct™, Oct. 16, 2007.

*Primary Examiner* — Heidi M Eide
(74) *Attorney, Agent, or Firm* — Knobbe, Martens, Olson & Bear, LLP.

(57) ABSTRACT

A dental implant is provided for supporting a dental prosthesis. The implant has a body having an outer surface, an apical end, a coronal end, a coronal portion, and a threaded portion. The coronal portion has a collar that tapers inwardly. The threaded portion has an intermediate portion and an apical portion, the intermediate portion tapering inwardly at a first angle and the apical portion tapering inwardly at a second angle. At least one thread is located on the outer surface of the threaded portion. The thread has a coronal flank, an apical flank, and a face extending between the coronal flank and apical flank.

25 Claims, 10 Drawing Sheets

(56) References Cited

U.S. PATENT DOCUMENTS

| | | |
|---|---|---|
| 2004/0063071 A1 | 4/2004 | Schroering |
| 2004/0219488 A1* | 11/2004 | Choi et al. .................... 433/173 |
| 2005/0164146 A1 | 7/2005 | Cantor |
| 2007/0099153 A1* | 5/2007 | Fromovich .................... 433/174 |
| 2008/0261175 A1 | 10/2008 | Hurson |
| 2009/0239195 A1* | 9/2009 | Wohrle et al. ................. 433/174 |

FOREIGN PATENT DOCUMENTS

| | | | | |
|---|---|---|---|---|
| FR | 2610512 | * | 2/1987 | ................ A61F 2/28 |
| WO | WO 01/49199 | | 7/2001 | |
| WO | WO 2004/103202 | | 12/2004 | |

* cited by examiner

COMPACT DENTAL IMPLANT

BACKGROUND OF THE INVENTION

1. Field of the Invention

The present invention generally relates to dental restoration and more specifically, to dental implants.

2. Description of the Related Art

Implant dentistry involves the restoration of one or more teeth in a patient's mouth using artificial components. Such artificial components typically include a dental implant and a prosthetic tooth, an abutment (single or multi-unit) and or a bridge or arch that is secured to the dental implant.

The dental implant is typically fabricated from pure titanium or a titanium alloy. The dental implant typically includes a body portion and a collar. The body portion is configured to extend into and osseointegrate with the alveolar bone. The top surface of the collar typically lies flush with the crest of the jawbone bone. The abutment (e.g., a final abutment) typically lies on the top surface and extends through the soft tissue, which lies above the alveolar bone. Recently, some dental implants have collars that extend above the crest of the jawbone and entirely through the soft tissue.

Implants of various tapers and with various thread profiles are known in the art. For example, U.S. Pat. No. 5,427,527 describes a conical implant design that is placed into a cylindrical osteotomy site in order to induce bone compression at the coronal aspect of the implant, i.e. at its widest end. Other thread profiles and patterns are known in the art. The most common design involves a symmetrical, V-shaped appearance such as that illustrated in U.S. Pat. No. 5,897,319. A variable thread profile is disclosed in U.S. Pat. Nos. 5,435,723 and 5,527,183 which is mathematically optimized for stress transfer under occlusal loads. U.S. Pat. Nos. 3,797,113 and 3,849,887 describe dental implants with external thread-like features having a flat shelf facing the coronal end of the implant.

While such prior art dental implants have been successful, there is a continuing desire to improve a dental implant's ability to osseointegrate with the alveolar bone and to improve the stability of the dental implant within the alveolar bone. For example, dental implants are often used to restore partially or completely edentulous patients and/or one or more teeth in the posterior region of the mouth. The posterior regions of the mouth often have less available bone height than the anterior regions. The bone density of the remaining bone after tooth loss can often be less in the posterior regions than the anterior region of the mouth.

SUMMARY OF THE INVENTION

One aspect of the invention is the recognition that merely using shorter dental implants that were originally configured for the anterior portions of the mouth does not optimally use the available bone in the posterior regions. Thus, a need exists for a dental implant that is particularly configured for use in the poster region of the mouth.

Accordingly, one embodiment comprises a dental implant for supporting a dental prosthesis that includes a body comprising an outer surface, an apical end, a coronal end, a threaded portion and a longitudinal axis. The coronal end of the body comprises a collar. The threaded portion comprises a coronal portion configured to engage cortical bone and an apical portion configured to engage cancellous bone. The threaded portion further includes at least one thread extending from a root surface, the at least one thread comprising a coronal flank, an apical flank, and a thread face that defines a length extending between the coronal flank and apical flank. The length of the thread face is smaller in the apical portion than the coronal portion of the thread and the thread has a thread depth $d3$ in the coronal portion of the thread that is less than a thread depth $d4$ in the apical portion of the thread and the coronal flank and the apical flank of the thread in the coronal portion form an angle that greater than an angle formed by the coronal flank and the apical flank of the thread.

An embodiment disclosed herein is a dental implant for supporting a dental prosthesis. The implant can comprise a body having an outer surface, an apical end, a coronal end, a coronal portion, a threaded portion, and a longitudinal axis. The coronal portion comprises a collar that tapers inwardly with respect to the longitudinal axis when viewed from the apical end to the coronal end. The threaded portion comprises an intermediate portion and an apical portion, the intermediate portion tapering inwardly at a first angle with respect to the longitudinal axis, the apical portion tapering inwardly at a second angle with respect to the longitudinal axis, where the first angle is greater than the second angle. At least one thread is located on the outer surface of the threaded portion. The thread has a coronal flank, an apical flank, and a face extending between the coronal flank and apical flank.

Another embodiment disclosed herein comprises a dental implant with a body comprising an outer surface, an apical end, a coronal end, a threaded portion and a longitudinal axis. The coronal end of the body comprises a collar. The threaded portion comprises a coronal portion, an intermediate portion and an apical portion. The threaded portion further comprises at least one thread extending from a root surface. The at least one thread comprises a coronal flank, an apical flank, and a face extending between the coronal flank and apical flank. The thread face has a thickness that generally increases from the coronal portion to the apical portion.

Further embodiments of the invention are defined by the dependent claims. These and other embodiments of the present invention will become readily apparent to those skilled in the art from the following detailed description of the preferred embodiments having reference to the attached FIGS., the invention not being limited to any particular preferred embodiment(s) disclosed.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures.

DETAILED DESCRIPTION OF THE PREFERRED EMBODIMENTS

Figure 1:
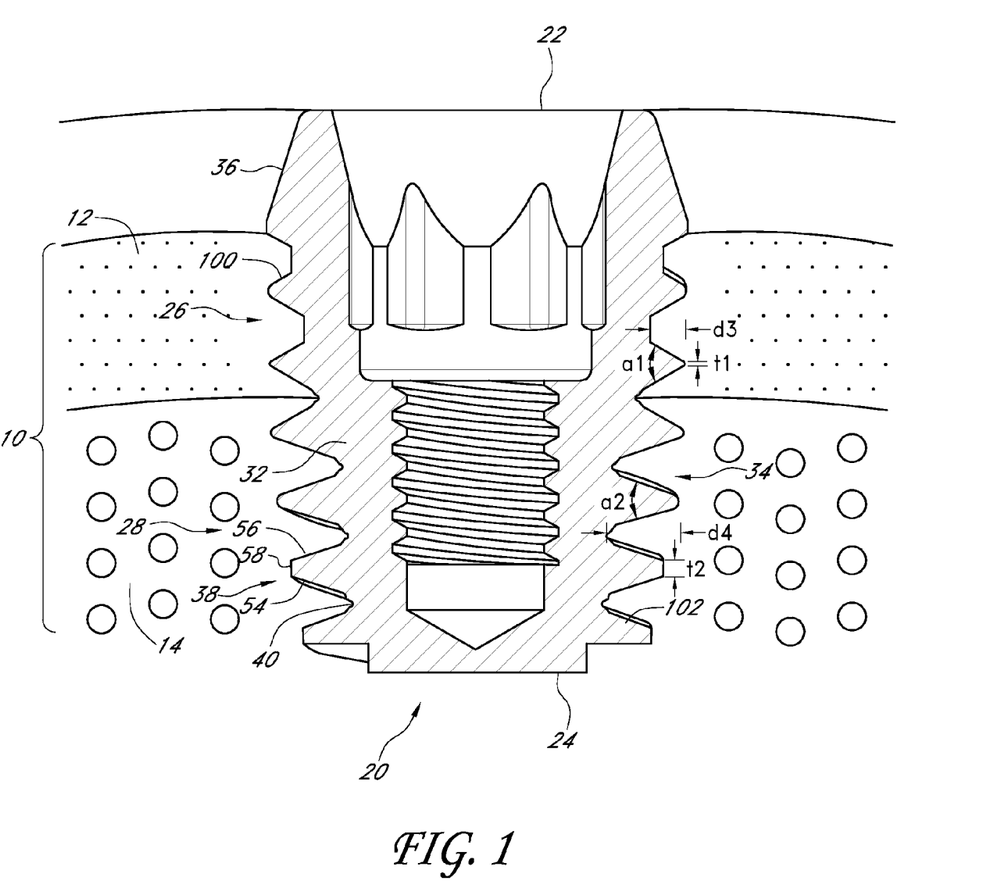
FIG. 1 is a cross-sectional side view of a dental implant that has been implanted in the patient's jawbone.

FIG. 1 illustrates an embodiment of a dental implant 20 that has been implanted into a patient's jawbone 10. The posterior region of the mandible can have less bone available for engaging the dental implant 20, and therefore, it is important to reduce the amount of bone absorption caused by the implantation of the dental implant 20. In addition, the patient's jawbone comprises an outer layer of hard, dense cortical bone 12 and an inner layer of spongy, porous cancellous bone 14. As will be explained below, the dental implant 20 is particularly configured for the posterior region of the mandible jaw where shorter implants may better support a prosthesis.

The dental implant 20 comprises a coronal end 22, a coronal portion 26 generally adjacent the coronal end 22, an apical end 24 and an apical portion 28 generally adjacent the apical end 24. As illustrated, the dental implant 20 also comprises an implant body 32, which includes a threaded portion 34 and a collar 36. The threaded portion 34 of the implant 20 can include a pair of threads 38 that are located on a root surface 40 of the threaded portion 34. Each of the threads 38 comprises an apical flank 54 and a coronal flank 56 that are connected by a thread face 58. At the base of each thread 38 is the root surface 40.

Figure 1A:
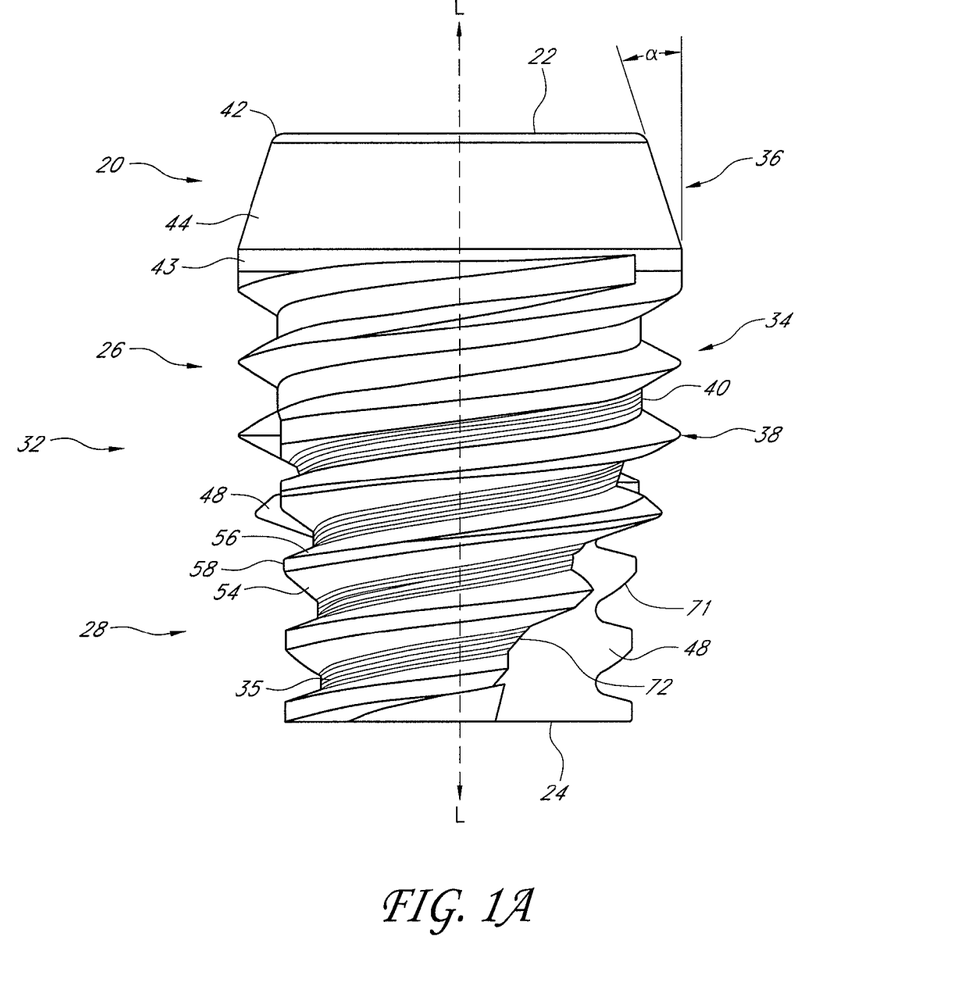
FIG. 1A is a side view of a dental implant in accordance with an embodiment of the present inventions.
Figure 1B:
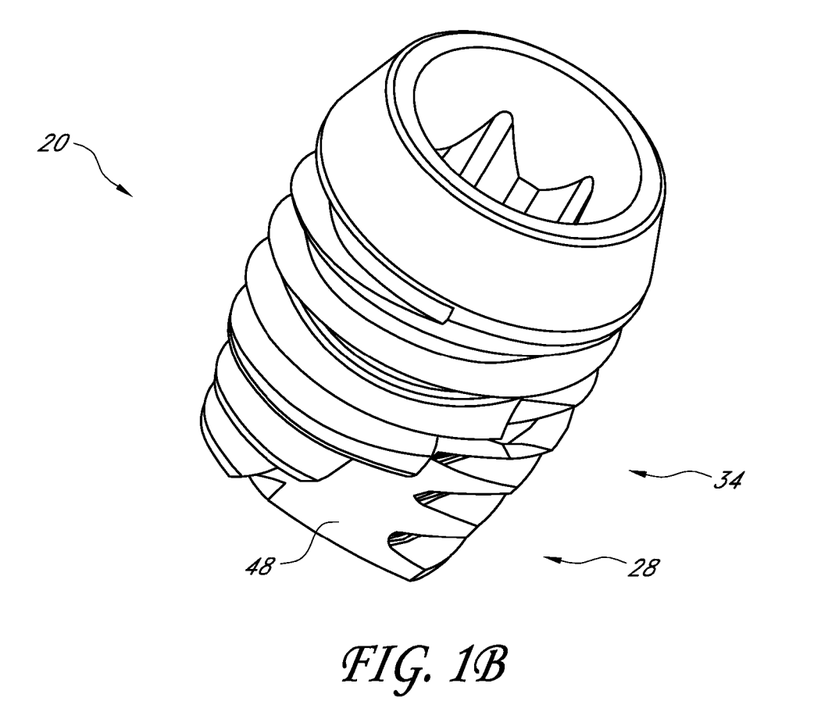
FIG. 1B is a perspective view of the dental implant of FIG. 1A.
Figure 1C:
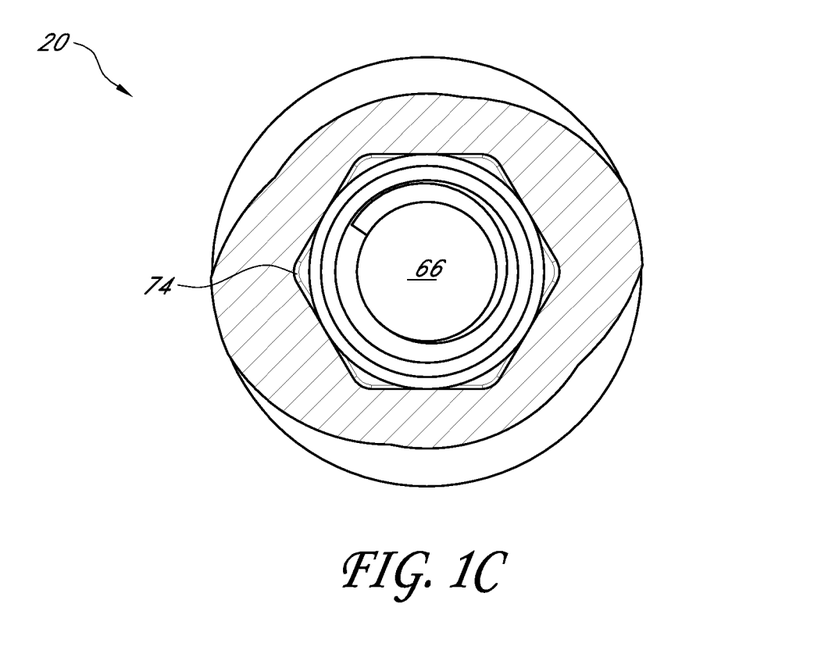
FIG. 1C is a cross-sectional top view of the dental implant of FIG. 1D taken along the plane E-E.
Figure 1D:
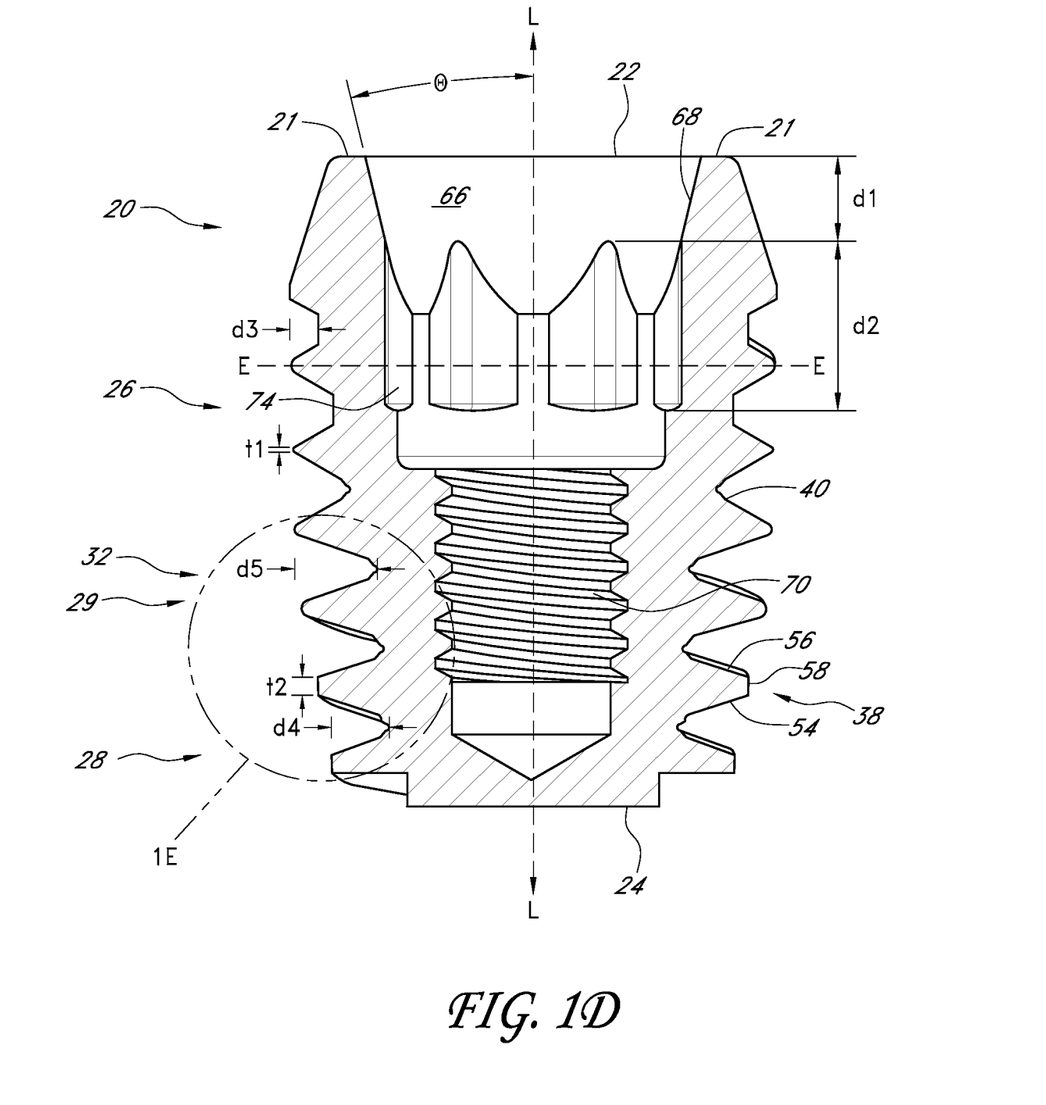
FIG. 1D is a cross-sectional side view of the dental implant of FIG. 1A.
Figure 1E:
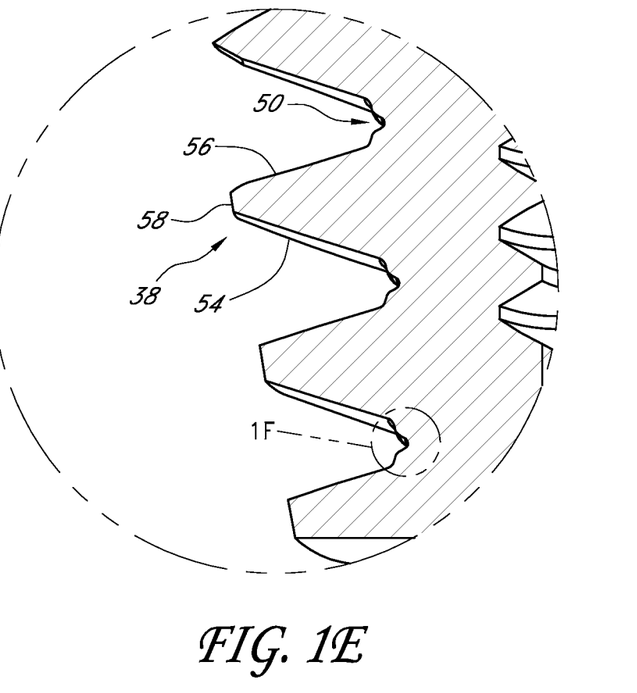
FIG. 1E is an exploded view of a portion of the dental implant of FIG. 1D enclosed in circle C.
Figure 1F:
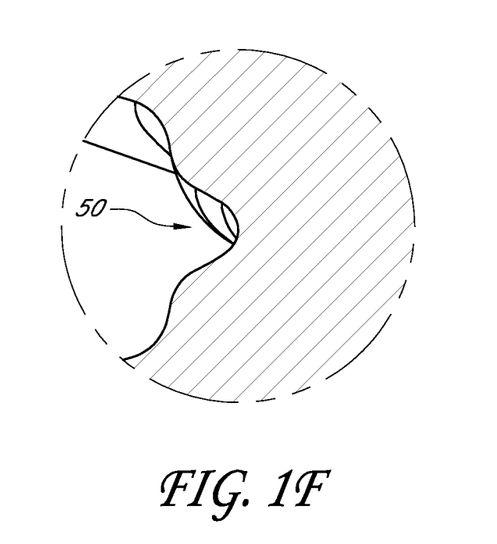
FIG. 1F is an exploded view of a portion of the dental implant of FIG. 1E enclosed in circle D.
Figure 1G:
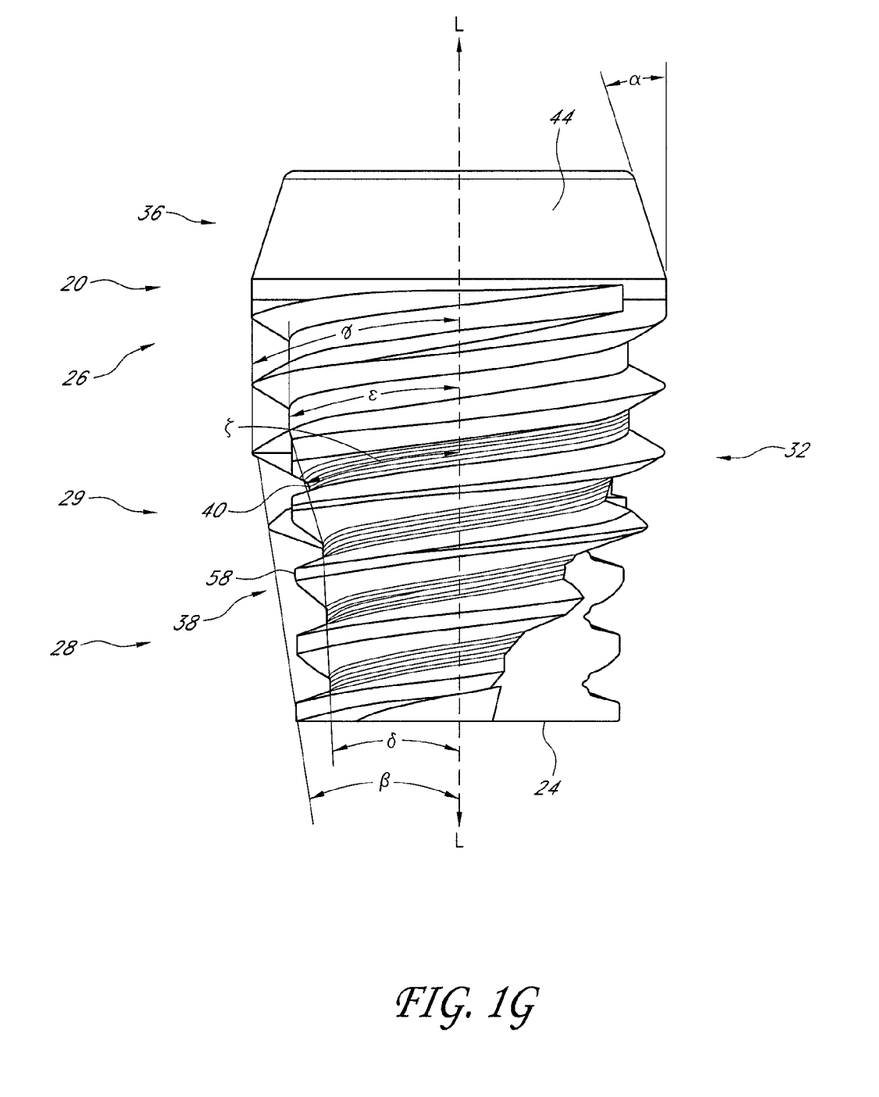
FIG. 1G is another side view of a dental implant of FIG. 1A.

In the preferred arrangement, as illustrated in FIGS. 1 and 1G, the threads 38 in the coronal portion 26 of the dental implant 20 comprise cortical threads 100 that are configured to engage the layer of cortical bone 12. In the apical portion 28 of the dental implant 20, cancellous threads 102, are configured to engage the layer of cancellous bone 14. Because the cortical bone 12 is hard and dense, the cortical threads 100 generally have a relatively shallow thread depth d3, as compared to the cancellous threads 102. Conversely, because the cancellous bone 14 is spongy and porous, the cancellous threads 102 generally have a relatively deep thread depth d4, as compared to the cortical threads 100. In some embodiments, the cancellous threads 102 can have a thread depth about 50% to about 100% greater than the cortical threads 100. In other words, the ratio d4/d3 ranges from about 1.5 to about 2. The greater thread depth of the cancellous threads 102 allows the cancellous threads 102 to penetrate deeper into the cancellous bone, which allows more surface area from the cancellous threads 102 to engage the cancellous bone, thereby forming a more stable connection as compared to shallow threads.

In some embodiments, the thread pitch, which can refer to the distance between threads 38, can be finer in the coronal portion 26 and coarser in the apical portion 28 of the implant 20. For an implant 20 with a single thread 38, the thread pitch is generally constant. For an implant 20 with two or more threads 38, the thread pitch of each of the threads 38, considered in isolation, is generally identical to the other threads 38 so that each thread 38 advances the implant 20 the same distance when the implant 20 is rotated in the patient's jawbone 10. However, when the implant 20 has for example two threads 38 that are evenly spaced apart, the thread pitch between the two threads, when measured as the distance between the first and second thread, is half of the thread pitch for a single thread 38 in isolation. Therefore, the thread pitch in the coronal portion 26 can be made relatively finer by adding an additional thread (not shown) to the coronal portion 26. For example, the implant 20 can have a single thread 38 that runs extends from the coronal portion 26 to the apical portion 28, and a second thread 38 that is located only in the coronal portion 26. In this manner, the effective thread pitch in the coronal portion 26 can be greater than the effective thread pitch in the apical portion 28 such that the finer threads engage the cortical bone while the coarse threads engage the cancellous bone. In yet another embodiment, four threads can be used in the coronal portion 26 while two threads can be used in the apical portion.

To further facilitate engagement with the cortical and cancellous bone portions respectively, the cortical threads 100 can be relatively wide with thread flanks 54 and 56 that form an angle a1 that can be about 60 degrees, while the cancellous threads 102 can be relatively thin with thread flanks 54 and 56 that form an angle a2 that can be about 35 degrees. In some embodiments, the angle a1 can be between about 50 degrees and about 70 degrees. In some embodiments, the angle a2 can be between about 25 degrees and 45 degrees.

In a similar manner, the cortical threads 100 are generally sharper than the cancellous threads 102 with faces 58 of the cortical threads 100 having a thickness t1 that is less than the thickness t2 of the cancellous threads 102. As illustrated, the thickness, t1, of the cortical threads 100 can approach zero, resulting in a face 58 that is essentially an edge. In this manner, shallow, sharp threads can be used to load the hard cortical bone 12 while deep, blunt threads can be used to load the soft cancellous bone 14. In one embodiment, the thickness t1 of the cortical threads 100 are about 0.1 mm or less while the thickness t2 of the cancellous threads are 0.1 mm or greater. In one embodiment, the thickness t1 ranges from about 0 mm to about 0.1 mm, and the thickness t2 ranges from about 0.1 mm to about 0.3 mm.

With continued reference to FIG. 1, the collar 36 can also be configured to engage the patient's gums. By making the collar outwardly tapering, the implant 20 displaces less gum tissue, thereby disturbing less tissue and preserving more of the patient's gums. In the illustrated embodiment, the collar 36 tapers to a diameter at the top surface 22 that is approximately equal to the largest diameter of a root surface 40 at the coronal end 26 of the implant 20. In one embodiment of use, the implant 20 is inserted into a hole formed in the bone that is approximately equal to the diameter of the root surface at the coronal end 26 of the implant 20. In this manner, lower portions of the collar 36 can be slightly larger than the hole in the bone and/or the overlaying gum tissue.

Accordingly, in the implant of FIG. 1, the threads 38 are optimized for the two different types of bone tissue. In this manner, the dental implant 20 can be made shorter and more effectively use the limited space available to form a secure connection with the bone tissue. In addition, the collar 36 is configured to be placed in the soft-tissue, such that threads 38 take advantage of the entire available cortical bone to add stability of the implant 20.

With reference now to FIGS. 1A-1G, the implant 20 of FIG. 1A will now be described in more detail. As shown, the compact dental implant 20 has a longitudinal axis L. In the illustrated embodiment, the implant 20 is about 6.5 mm in length when measured from the coronal end 22 to the apical end 24. In other embodiments, the implant 20 can be between about 5 mm and 8 mm, or between about 5.5 mm and 7.5 mm, or between about 6 mm and 7 mm in length. The diameter of the coronal end 22 can be between about 3 mm to 5 mm, or about 4 mm, or about 4.1 mm. The diameter of the apical end 24 can be between about 2 mm to 5 mm, or about 4 mm, or about 3.9 mm. The height of the collar 36 when measuring along the longitudinal axis L can be between about 1 mm to about 2 mm, or about 1.5 mm. The diameter of the apical portion of the collar 36 can be between about 3 mm to 6 mm, or about 5 mm, or about 4.9 mm. The height of the threaded portion 34 can be between about 3 mm and 7 mm, or between about 4 mm and 6 mm, or about 5 mm. As described above, the illustrated embodiment of the dental implant 20 is particularly useful when the depth of the jawbone is relatively shallow since the dental implant 20 generally has less available penetration depth than standard dental implants in order to be securely implanted into the patient's jawbone. As described above, the threaded portion and the collar 36 are configured to optimally use the available penetration depth in the posterior region to promote retention and inhibit bone resorption. In addition, the collar 36 can be configured to engage the patient's soft tissue, such as the patient's gums.

As will be explained below, although the illustrated embodiment includes a pair of threads 38 that each extends helically around the implant 20, modified embodiments may include more or less threads. In addition, as explained below, a surface formed by faces 58 of the threads 38 and/or the root surface 40 can be generally conical or taper inwardly in the apical direction. In some embodiments, the surface formed by faces 58 of the threads 38 and/or the root surface 40 comprises at least two different tapers, as explained below. However, in other embodiments, the surface formed by faces 58 of the threads 38 and/or the root surface 40 can be substantially cylindrical or otherwise shaped. The implant 20 may be made of titanium, although other materials may be used, such as various types of ceramics, plastics or composites.

In the description herein, reference will be made to various structures that "taper" "inwardly." Unless otherwise specified, tapering inwardly means that the surface of the referenced structure generally lies closer to the longitudinal center of the dental implant 20 as the structure moves towards the apical end 24 of the implant 20. Accordingly, "tapering outwardly" means that the surface of the referenced structure generally lies further from the longitudinal center of the implant 20 as the structure moves to the apical end of the implant 20. Thus, with reference to FIG. 1A, in the illustrated embodiment, the collar 36 generally tapers outwardly while the threaded portion 36 generally tapers inwardly.

In the illustrated embodiment, the implant body 32 includes an outer surface or a bone apposition surface 40, which can be configured to promote osseointegration. In one embodiment, the bone apposition surface 40 is configured to promote osseointegration by increasing the surface area of the body 32. In this regard, the bone apposition surface 40 can be formed by roughening the implant body 32 in several different manners, such as, for example, by acid-etching, grit blasting, and/or machining. Alternatively, the bone apposition surface 40 can be formed by coating the lower surface with a substance in order to promote osseointegration. In some embodiments, this may result in decreasing or increasing the surface area of the implant body 32. Calcium phosphate ceramics, such as tricalcium phosphate (TCP) and hydroxyapatite (HA) are examples of materials that can enhance osseointegration by changing the chemistry of the outer surface 40. In other embodiments, the outer surface 40 can comprise macroscopic structures, such as, for example, threads, micro-threads, indentations, and/or grooves that are configured to promote osseointegration and can be used alone or combined with the roughening and/or the coatings described above. In one embodiment, the outer surface 40 comprises a microstructure surface, such as, a highly crystalline and phosphate enriched titanium oxide microstructured surface with open pores in the low micrometer range. An example of such a surface is sold under the trademark, TiUnite™ by Nobel Biocare AB. In another embodiment, the body 32 can be form from a zirconium ceramic or other ceramic material that can be coated with porous zirconium to provide a microstructure surface. In another embodiment, the microstructure surface can be coated with a substance configured to promote osseointegration (such as BMP).

With continued reference to FIG. 1A, the collar 36 can lie coronal to the threaded portion 34 and, in the illustrated embodiment, can be integrally formed with or permanently affixed to the threaded portion 34. The collar 36 can be defined at least in part by a sidewall 44. In the illustrated embodiment, the sidewall 44 tapers outwardly in an apical direction at approximately an angle that is $\alpha$ degrees, with respect to the longitudinal axis L. In some embodiments, $\alpha$ is between approximately 0 degrees and 30 degrees, or between approximately 0 degrees and 20 degrees.

In some embodiments, the coronal portion of the collar 36 has a beveled or chamfered edge 42. The chamfered edge 42 can be oriented at an angle between about 30 degrees and 60 degrees, or preferably about 45 degrees with respect to the longitudinal axis L. The height of the chamfered edge 42 when measuring along the longitudinal axis L can be between about 0.05 mm to about 0.3 mm, or preferably about 0.1 mm. In some embodiments, the apical portion of the collar 36 can comprise a cylindrical portion 43 that is generally adjacent the threaded portion of the implant body 32. The height of the cylindrical portion 43 can be between about 0.05 mm and 0.3 mm, or between about 0.2 mm. By making the collar 26 outwardly tapering, the implant 20 displaces less gum tissue, thereby disturbing less tissue and preserving more of the patient's gums.

As mentioned above, the outwardly tapering collar 36 can be configured to engage soft tissue, such as the patient's gums. The collar 36 can have a textured or smooth surface. A smooth surface can reduce plaque or tarter buildup on the surface of the collar 36, while a rough surface can promote soft tissue engagement to the collar 36 which can result in a more aesthetic appearance. The diameter of the outwardly tapering collar 36 can be matched to the size of an abutment to be used in conjunction with the dental implant 20. For example, in some embodiments, the diameter of the coronal end 22 is between about 3 mm to 5 mm, or about 4 mm, or about 4.1 mm, and the diameter of the apical portion of the collar 36 is between about 3 mm to 6 mm, or about 5 mm, or about 4.9 mm. The size and shape of the collar can be varied to match a variety of platform sizes.

In modified embodiments, the collar 36 can be provided with grooves as described in U.S. patent application Ser. No. 11/739,034, the entirety of which is incorporated herein by reference. In other embodiments, circumferential protrusions or micro-threads can be provided on the collar 36.

In the embodiment shown in FIGS. 1A-1G and as noted above, each of the threads 38 comprises an apical flank 54 and a coronal flank 56 that are connected by the face 58. At the base of each thread 38 is the root surface 40. As mentioned above the illustrated dental implant 20 includes a pair of threads 38 that begin at opposing sides of the apical end 24 and progress towards the coronal end 22 along the threaded portion 34 while maintaining opposing positions along the threaded portion 34 of the implant body 32. Accordingly, in the illustrated embodiment each of the threads 38 has about the same distance between the faces 58 of a particular thread 38. In the illustrated embodiment, the threads 38 have a pitch of about 1.6 mm, which, as is in conventional in the art, defined as the axial distance between successive thread peaks.

In other embodiments, the threads 38 have a pitch between about 0.5 mm and 2.5 mm, or between 1 mm and 2 mm. It will be appreciated that, although the illustrated embodiment shows two threads 38, other suitable numbers of threads 38 may also be used, such as one or three. In general, if multiple threads 38 are used, the beginning locations of the threads 38 are spaced about evenly around the apical end 24 from each other. In addition, as mentioned above, in some embodiments, the coronal portion 26 can include a larger number of threads than the apical portion 28 such that the effective pitch is finer in the coronal portion 26.

As illustrated in FIG. 1G, the thread faces 58, the side wall 44 and the root surface 40 can define a plurality of different angles with respect to the longitudinal axis L: a first angle α can be defined by the sidewall 44 of the collar 36 as described above; a second angle β can be defined by the faces 58 of the threads 38 on the apical portion 28 of the body 32; a third angle γ can be defined by the faces 58 of the threads 38 on the coronal portion 26 of the body 32; a fourth angle δ can be defined by the root surface 40 on the apical portion 28 of the body 32; a fifth angle ε can be defined by the root surface 40 on the coronal portion 26 of the body 32; and a sixth angle ζ can be defined by the root surface 40 in an intermediate portion 29 of the implant body 32 in between the coronal portion 26 and the apical portion 28.

In some embodiments, the first angle α can be between about 0 degrees to 30 degrees, or between about 0 degrees to 20 degrees; the second angle β can be between about 0 degrees to 30 degrees, or between about 0 degrees to 15 degrees, the third angle γ can be between about 0 degrees to 30 degrees, or between about 0 degrees to 15 degrees; the fourth angle δ can be between about 0 degrees to 30 degrees, or between about 0 degrees to 15 degrees; the fifth angle ε can be between about 0 degrees to 30 degrees, or between about 0 degrees to 15 degrees; and the sixth angle ζ can be between about 0 degrees to 45 degrees, or between about 0 degrees to 30 degrees.

With reference to FIG. 1G, in some embodiments the tapered shape of the root surface 40 can comprise a variable angle as described above. The variable angle can vary such that the angle at the apical portion 28 of the root surface 40 with respect to the longitudinal axis can be more tapered, about the same taper, or less tapered than that at the coronal portion 26. Further, the surface formed by the faces 58 of the threads 38 can define a varying conical angle as described above. The angle defined by the faces 58 of the threads 38 can be different from the varying conical angle formed by root surface 40. That is, the conical angle defined by the root surface 40 of the implant body 32 can be steeper or more tapered with respect to the longitudinal axis than the conical angle formed by faces 58 of the threads 38. In one embodiment, the conical angle defined by the root surface 40 of the implant body 32 can be greater than the conical angle formed by faces 58 of the threads 38. In another embodiment, the conical angle defined by the root surface 40 of the implant body 32 can about the same as the conical angle formed by faces 58 of the threads 38. Although the illustrated embodiment utilizes the aforementioned conical angle relations, other suitable relations may be used. Such suitable relations may comprise threads 38 in which the faces 58 define a generally cylindrical shape and/or where the faces 58 of the threads 38 that define a conical angle that closely matches the conical angle of the root surface 40 of the implant body 32. In still other embodiments, the angle defined by the faces 58 of the threads 38 and/or the angle defined by the root surface 40 can be generally parallel to the longitudinal axis of the implant 20 such that they are substantially cylindrical. In this manner, the implant 20 is advantageously configured to more effectively use the available bone and, in particular, provide the most effective thread configuration for each type of bone.

With reference to FIG. 1A and FIG. 1B, in the illustrated embodiment, the threaded portion 34 of the dental implant 20 comprises two flutes 48 that are positioned on the apical portion 28 of the dental implant 20. The flutes 48 are configured to aid in inserting the dental implant 20. The flutes 48 can comprise a generally helical shape. Further, the flutes 48 can extend from the apical end 24 towards the coronal portion 26 of the dental implant 20. The flutes 48 can be located at generally opposing positions along the threaded portion 34 of the implant body 32. In some embodiments, each flute 48 makes between about a 30 degree to 150 degree turn, or between about a 60 degree to 120 degree turn, or about a 90 degree turn. In the illustrated embodiment, the flutes 48 are configured to cut, or remove bone, when the dental implant 20 is rotated in a counterclockwise direction. Furthermore, the flutes 48 are configured to allow the dental implant 20 to be rotated clockwise without cutting or removing bone. Accordingly, in the illustrated embodiment, the flute 48 includes a leading edge 71 that provides minimal cutting and acts as an auger as the implant 20 is rotated into the bone. The trailing edge 72, in turn, provides a cutting surface that can be used to remove bone if the implant 20 is rotated counter-clockwise.

Although the illustrated embodiment of the dental implant 20 has been shown with flutes 48 that are configured to cut when the dental implant 20 is rotated in a counterclockwise direction, other suitable flutes or flute orientations may also be used. Such suitable flutes or flute orientations may comprise flutes that are configured to cut or provide a tapping function when the dental implant 20 is rotated in a clockwise direction.

Figure 4:
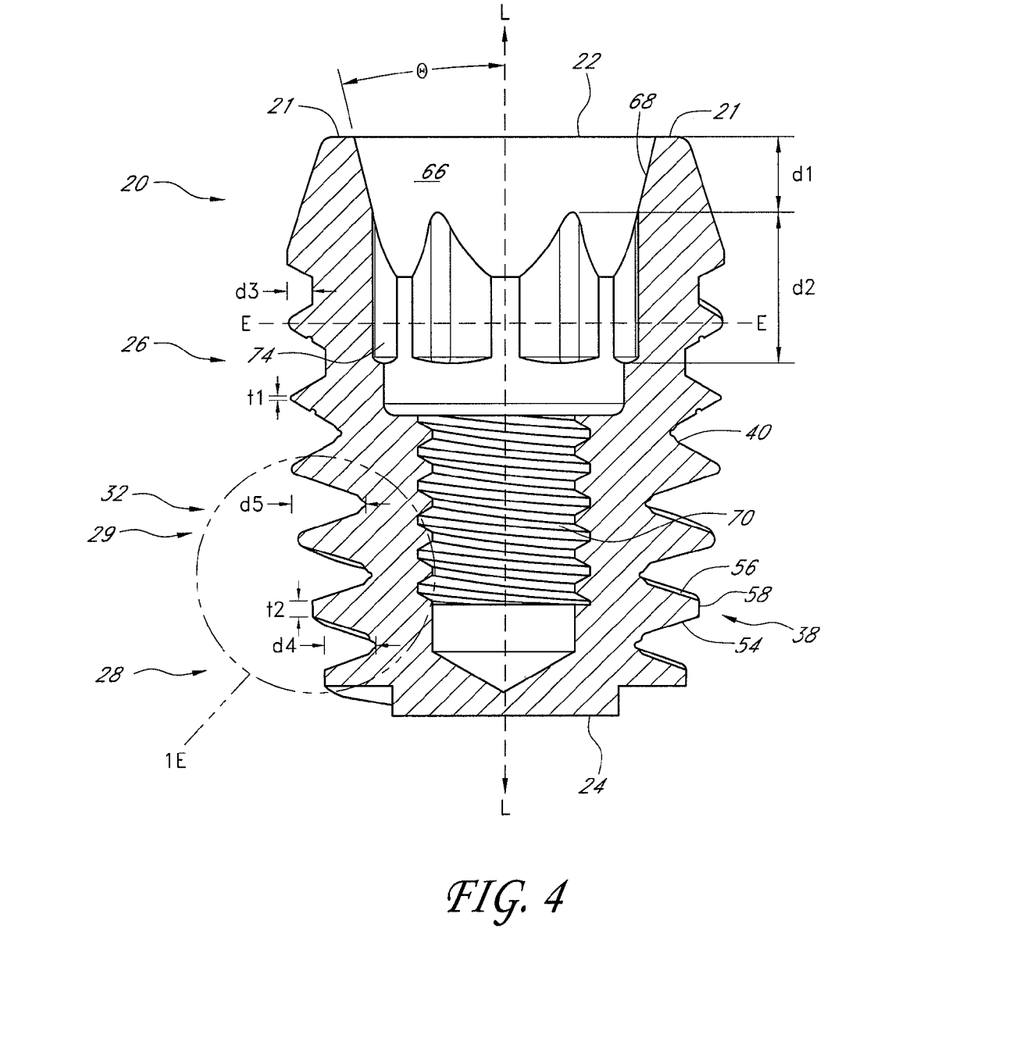
FIG. 4 is a side view of another embodiment of a dental implant.

As illustrated in FIG. 1A, FIG. 1E and FIG. 1F, in one embodiment the threaded portion 34 also comprises grooves 50 that are located on the implant body 32 between each pair of threads 38 in the apical portion 28 of the implant 20. In some embodiments as illustrated FIG. 4, the grooves 50 can be located on the apical flank 54 of the threads in the coronal portion 26 of the implant 20. The groove 50 between the threads 38 can also extend into the coronal portion 26 while the groove 50 on the apical flank 54 can extend into the apical portion 28.

In general, the grooves 50 extend in a generally helical pattern. In the illustrated embodiment which has two grooves 50, each groove 50 is substantially continuous. However, in modified embodiments, one or both grooves 50 can be formed to be non-continuous. For example, the grooves 50 can be formed from a series of shorter grooves, dimples, or indentations that together form a generally helical pattern. However, continuous grooves can advantageously promote bone attachment as growth as it has been observed that bone tissue likes to grow along continuous channels.

As illustrated in FIG. 1E and FIG. 1F, the grooves 50 have a cross-sectional shape that tapers inwardly to a rounded bottom portion. In the context of grooves 50, an inward taper refers to a generally v-shaped cross-section, where the top portion of the groove 50 is wider than the bottom portion, and an outward taper refers to a generally inverted v-shaped cross-section, where the top portion of the groove 50 is narrower than the bottom portion. In some embodiments, the groove 50 may not taper or may taper outwardly. In other embodiments, the bottom portion of the groove 50 may not be rounded, and instead, may be flat or a point. In some embodiments, the top portion of the groove 50 is between about 0.025 mm to about 0.4 mm wide, or between about 0.05 mm to 0.2 mm wide, or about 0.1 mm wide. In some embodiments, the rounded bottom portion has a radius of curvature between about 0.01 mm to 0.06 mm, or between about 0.015 mm to 0.045 mm, or about 0.03 mm. In some embodiments, the groove 50 is between about 0.02 mm to 0.2 mm deep, or about 0.04 to 0.14 mm deep, or about 0.07 mm deep.

With continued reference to FIG. 1A, FIG. 1E and FIG. 1F, the grooves 50 are located on the dental implant 20 to, e.g. provide additional surfaces for osseointegration. The grooves 50 can begin at the apical end 24 of the dental implant 20 and can be formed between the pair of threads 38 on the outer surface 35 of the apical portion 28 of the implant body 32. The grooves 50, in the illustrated embodiment, can extend toward the coronal end 22 of the implant 20 over a substantial portion of the apical portion 28. In the coronal portion 26, grooves 50 can extend on the apical face 54 of the threads 38. In modified embodiments, the grooves 50 in the coronal portion 26 can extend on the face 58 and/or coronal portion 56 of the threads 38 in addition to or in the alternative to the illustrated arrangement. In a similar manner, the grooves in the apical portion 28 can be on the face 58, apical portion 58, and/or coronal portion 56 of the threads. As mentioned above, the grooves 50 between the pair of threads 38 can overlap axial with the grooves formed on the apical face 54 of the threads 38 such that a portion of the implant 20 includes both grooves 50.

The outer surface 35 can be formed such that the grooves 50 dissipate and/or taper toward the coronal end 22 of the implant 20. The dissipation and/or tapering of the grooves 50 can occur over a distance approximately within a ¼-½ rotation of the implant 20, although in other embodiments the distance can be greater or less than ¼-½ rotation. In some embodiments, the portion of the outer surface 35 between the threads beyond the dissipation and/or taper will not include the grooves 50.

The grooves 50 can be sized such that the grooves 50 occupy only a portion of the outer surface 35 of the apical portion 34 between the threads 38. It will be appreciated that in other embodiments the grooves 50 may be sized such that they occupy substantially all of a portion of the outer surface 35 between the threads 38. Additionally or alternatively the grooves 50 can be formed on the faces 58 and/or upper flanks 56 and/or lower flanks 54 of the threads 38.

As seen in FIG. 1C and 1D, the dental implant 20 can also comprise a cavity or internal connection interface 66 that is open at the coronal end 22 of the dental implant 20. In the illustrated embodiment, the cavity 66 comprises a conical chamber 68, a hexagonal interlock recess 74 and a threaded chamber 70. The conical chamber 68 and interlock recess 74 can be configured to receive an abutment and the threaded chamber 70 can be configured to receive a coupling screw.

The threaded chamber 70 can be located generally below the abutment chamber 68. As was mentioned above, the threaded chamber 70 can be configured to receive a coupling screw (not shown) that is configured to attach an abutment to the implant 20.

Although the particular embodiment shown in FIGS. 1A-1D has been shown with a conical chamber 68 and a generally hexagonal shaped interlock recess 74, other suitable shapes and styles of recesses may also be used (e.g., square, non-round, and other shapes). Furthermore, it may be appreciated by one skilled in the art, that some embodiments of the dental implant 20 may omit a cavity 66 all together and may use an external coupling device (e.g., an external hex) and/or an integrally formed abutment. With respect to the illustrated embodiment, additional details and modified embodiments of the cavity 66 can be found in Applicant's co-pending application filed on the same date as this application under U.S. application Ser. No. 11/739,024, filed Apr. 23, 2007, entitled "DENTAL IMPLANT AND DENTAL COMPONENT CONNECTION," the entirety of which is also incorporated herein by reference.

The illustrated socket 66 is advantageously configured to provide an enhanced connection interface and to provide flexibility such that the implant 20 can mate with multiple types of dental components. In particular, as noted above, the conical portion 68 comprises a side wall that tapers inwardly with respect to the longitudinal axis L of the implant 20 providing a wider initial opening for the socket 66. With reference to FIG. 1D, the particular geometry of the conical chamber 68 defines a conical half angle θ with respect to the longitudinal axis L. In one embodiment, the conical half angle is between about 5 degrees and about 20 degrees. That is, the angle between the inner wall 80 of the conical chamber 68 and a longitudinal center line L preferably is between about 5 degrees and about 20 degrees. In one embodiment, the conical half angle is about 12 degrees.

In one embodiment, the ratio between the length (d1) of the conical portion 68 and the length (d2) the interlock recess 74 is about 1:2. In one preferred embodiment, the depth (d1) of the conical chamber 68 is at least about 0.8 mm and the depth (d2) of the interlock recess 74 is at least about 1.6 mm. As shown in FIG. 1D, the length (d1) of the conical portion 68 is a distance measured in a vertical direction from the top surface 21 of the implant 20 to the portion of the socket 66 in which the tapered surfaces 80 of the conical portion 68 terminate. The length (d2) of the interlock recess 74 is measured in a vertical direction from the end of the conical portion 68 to the end of the interlock recess 74. The ratios and length of the conical portion 68 and the depth and length of the interlock recess 74 advantageously combine the benefits of a sufficiently long tapered connection to provide an effective seal with a sufficiently long interlock recess 74 such that a sufficient driving torque can be transmitted to the implant 20, when the implant is driven into the patient.

Yet another advantage of the illustrated embodiment is an area or thickness of the substantially planar top surface 21 of the implant 20. In one embodiment, the top surface 21 of the implant 20 advantageously can provide a surface to support certain dental restorations on the top surface 21 of the implant 20. Additionally or alternatively, the top surface 21 can be used to support a component that bypasses the interlock recess 74. Accordingly, in one embodiment, the top surface 21 of the implant 20 has at least a thickness as measured between the outer and inner periphery of the top surface 21 that is greater than at least about 0.2 mm and in another embodiment greater than at least about 0.3 mm. In one embodiment, the thickness of the top surface 21 is about 0.38 mm.

The embodiments described above provide for improved stability of a dental implant when implanted in the alveolar bone. Furthermore, certain embodiments of the invention provide efficient utilization of space. For example, as described above, in the coronal portion 26 the groove 50 can be located on the thread 38 (on the face 58, coronal portion 56, and/or apical portion 54) of the body 32 containing the internal connection interface 66. Hence, the strength of the body of the implant 20 at this location remains unaffected. If the groove 50 had been located on the body 32 at this portion, less space would have been available for the internal connection interface 66 with maintained minimum wall thickness at specific dimensions to maintain body strength. Hence, having the groove 50 positioned as described above improves the space available for the connection interface 66 and still provides for improved stability of the implant 20. In some embodiments, the wall thickness will be sufficient if the groove 50 is located at the face 58 only at the portion of the interlock recess 74 but at least partly not at the location of the threaded chamber 70.

As illustrated in FIG. 1G, in the portion of the body 32 that does not include the internal connection interface 66, the groove can be located on the body 32. This will not deteriorate the strength of the implant 20 substantially as the implant 20 of the illustrated embodiment does not include any internal recess 66 at this portion. This provides for the option of having a thinner face of the thread 38 at this location, such as a variable thread thickness, which may provide for even further improved stability of the implant 20. Hence, the location of the groove 50 provides for stability themselves as well as their specific locations. In addition, efficient utilization of the space available without compromising strength is provided. The locations also provides for flexibility, as the locations for the grooves 50 can be used on implants having either an internal connection interface 66 or an external connection interface.

Figure 2A:
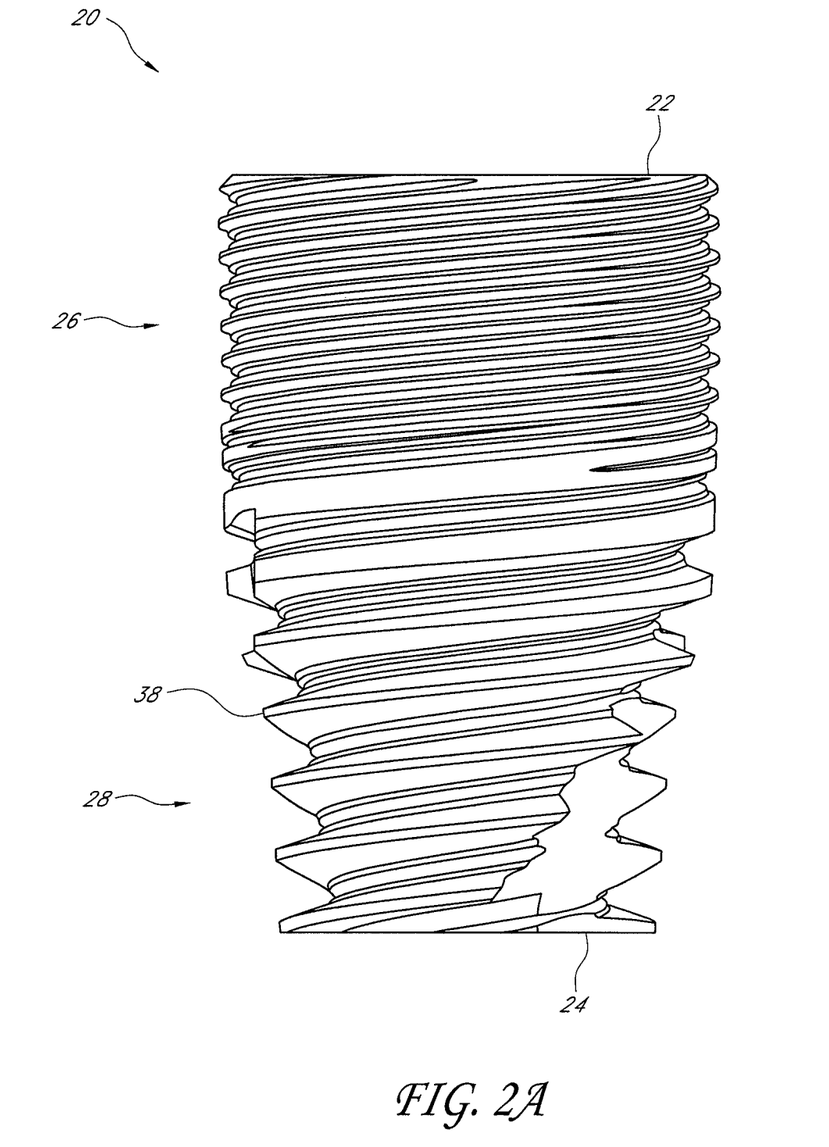
FIG. 2A is a side view of another embodiment of a dental implant.
Figure 2B:
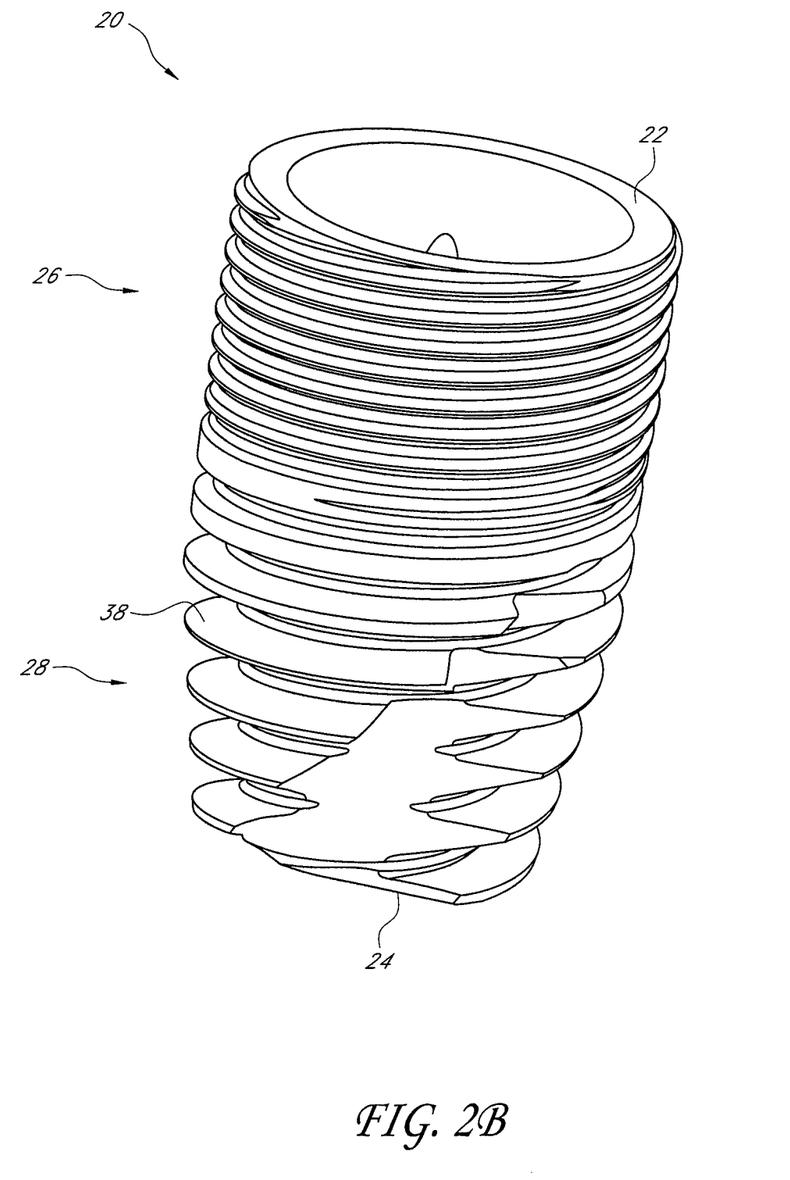
FIG. 2B is a perspective view of the dental implant of FIG. 2A.

FIGS. 2A and 2B illustrate another embodiment of the dental implant 20 that is particularly suitable for use as a bone level implant. This embodiment of the dental implant 20 lacks a collar, and therefore, the dental implant 20 is configured to be disposed substantially entirely within the patient's jawbone. The dental implant has a coronal end 22, an apical end 24, a coronal portion 26 and an apical portion 28.

As illustrated, the dental implant 20 has double threads 38, spaced evenly apart and having the same pitch, that extend from the apical end 24 to the coronal end 22 of the dental implant 20. In addition, two additional threads 38, having the same pitch as and spaced evenly apart from the first set of threads 38, are located on the coronal portion 26 of the implant 20. Therefore, the coronal portion 26 is quadruple threaded while the apical portion 28 is double threaded. This results in a finer threaded coronal portion 26 that engages the cortical bone, and a coarser threaded apical portion 28 that engages the cancellous bone. In addition, as described above, the thread depth in the coronal portion 26 is substantially shallower than the thread depth in the apical portion 28 of the dental implant 20. For example in one embodiment, the thread depth in the coronal portion 26 between about 0.2 to about 0.15 millimeters and in the apical portion 28 the thread depth can be between about 0.6 to about 0.7 millimeters. In one embodiment, the diameter at the coronal portion of the implant is about 4.3 millimeters.

Figure 3:
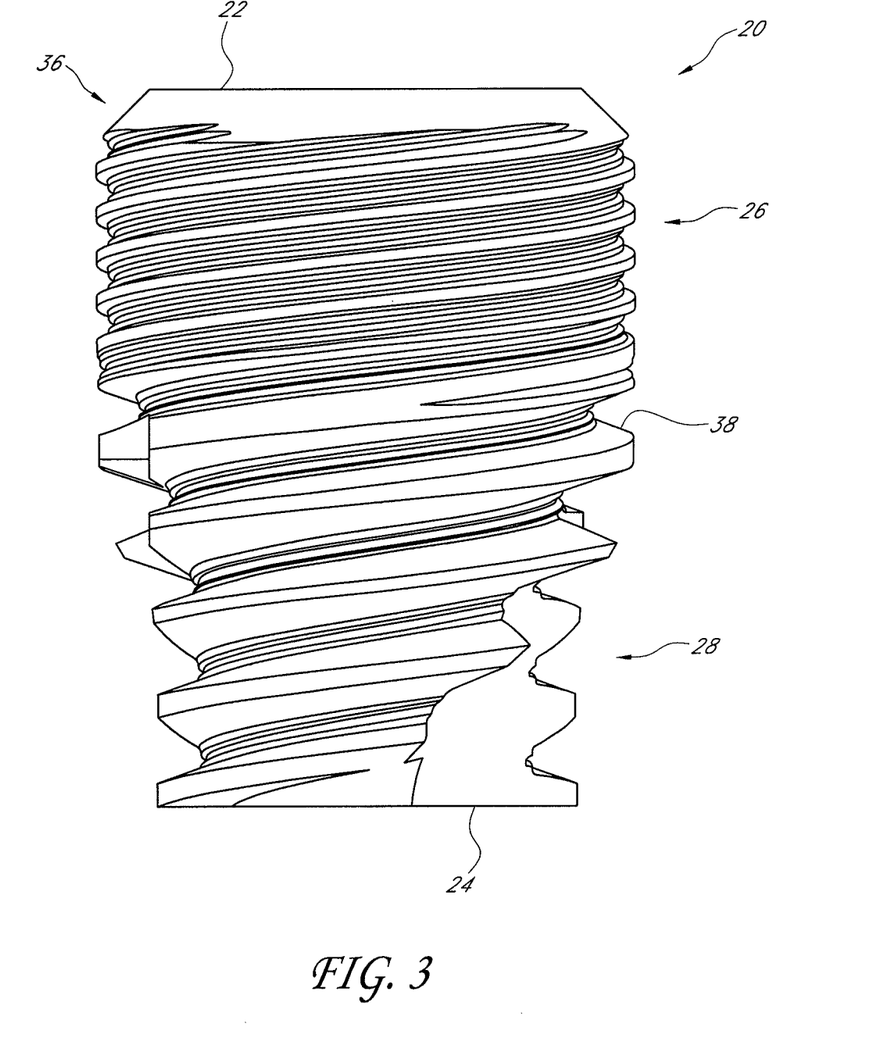
FIG. 3 is a side view of another embodiment of a dental implant.

FIG. 3 illustrates another embodiment of a dental implant that is similar to the embodiment of FIGS. 2A and 2B. In this embodiment, the implant 20 has a short beveled collar 36 with a height of about 0.5 millimeters. As with the previous embodiment, this implant can be positioned substantially at bone level. In one embodiment, the implant can have a diameter of about 5.0 millimeters at the collar 36.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof In addition, while the number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with, or substituted for, one another in order to perform varying modes of the disclosed invention. Thus, it is intended that the scope of the present invention herein disclosed should not be limited by the particular disclosed embodiments described above, but should be determined only by a fair reading of the claims.

What is claimed is:

1. A dental implant for supporting a dental prosthesis, the implant comprising:
    a body comprising an outer surface, an apical end, a coronal end, a threaded portion and a longitudinal axis, the coronal end of the body comprising a collar, the threaded portion comprising a coronal portion configured to engage cortical bone and an apical portion configured to engage cancellous bone, the threaded portion further comprising at least one thread extending from a root surface that forms a longitudinal side of the body, the at least one thread comprising a coronal flank, an apical flank, and a thread face that defines a length extending between the coronal flank and apical flank, wherein the length of the thread face is larger in the apical portion than the coronal portion and the thread has a thread depth d3 in the coronal portion of the thread that is less than a thread depth d4 in the apical portion and the coronal flank and the apical flank in the coronal portion form an angle that is greater than an angle formed by the coronal flank and the apical flank in the apical portion and wherein the thread face of at least a portion of the at least one thread is substantially flat.

2. The dental implant as in claim 1, wherein the ratio d4/d3 is between about 1.5 to about 2.

3. The dental implant of claim 1, wherein the coronal flank and the apical flank of the thread in the coronal portion form an angle that is between about 50 and 70 degrees, and the coronal flank and the apical flank of the thread in the apical portion form an angle that is between about 25 and 45 degrees.

4. The dental implant of claim 1, wherein the length of the thread face in the coronal portion is equal to or less than about 0.1 millimeters and the length of the thread face in the apical portion is greater than or equal to 0.2 millimeters.

5. The dental implant of claim 1, wherein a length of the dental implant when measured from the coronal end to the apical end is between about 6 to 7 mm.

6. The dental implant of claim 5, wherein the collar of the dental implant tapers outwardly with respect to the longitudinal axis of the dental implant.

7. The dental implant of claim 5, wherein a maximum diameter of the root surface in the coronal portion is approximately equal to a minimum diameter of the collar.

8. The dental implant of claim 1, further comprising a groove formed on the outer surface of the body and located between adjacent apical and coronal flanks.

9. A dental implant for supporting a dental prosthesis, the implant comprising:
    a body comprising an outer surface, an apical end, a coronal end, a coronal portion, a threaded portion and a longitudinal axis, the coronal portion of the body comprising a collar, the collar tapering outwardly with respect to the longitudinal axis, the threaded portion comprising a coronal portion, an intermediate portion and an apical portion, the threaded portion further comprising at least one thread extending from a root surface, the at least one thread comprising a face that forms a thread face surface,
    in the intermediate portion of the threaded portion, the root surface tapering inwardly at a first angle with respect to the longitudinal axis, in the apical portion of the threaded portion the root surface tapering inwardly at a second angle with respect to the longitudinal axis, the first angle being greater than the second angle;

the at least one thread comprising a coronal flank, an apical flank, and the face extending between the coronal flank and apical flank.

10. A dental implant as in claim 9, wherein in the coronal portion of the threaded portion, the root surface tapers inwardly at a third angle less than the first angle.

11. A dental implant as in claim 9, wherein in the coronal portion of the threaded portion the thread face surface tapers inwardly at a fourth angle and in the apical portion of the threaded portion the thread face surface tapers inwardly at a fifth angle that is greater than the fourth angle.

12. The dental implant of claim 9, further comprising a groove formed on the outer surface of the body and located between adjacent apical and coronal flanks.

13. The dental implant of claim 9, comprising a groove having a helical pattern, the groove being formed on at least a portion of the coronal flank or apical flank of the thread.

14. The dental implant of claim 9, further comprising a cavity located at least partially in the coronal portion of the body, the cavity being open towards the coronal end of the dental implant and configured to attach an abutment.

15. The dental implant of claim 9, comprising a first groove having a helical pattern, the first groove being formed on at least a portion at least one of the coronal or apical flank of the thread and a second groove having a helical pattern, the second groove being formed on at least a portion of the body adjacent the coronal and apical flanks.

16. The dental implant of claim 15, wherein the first groove is continuous.

17. The dental implant of claim 15, wherein the first groove is formed as a series of dimples.

18. The dental implant of claim 15, wherein the second groove is continuous.

19. The dental implant of claim 9, wherein the dental implant further comprises at least one flute located on the implant.

20. The dental implant of claim 9, comprising a first groove having a helical pattern, the first groove being formed on at least a portion of the thread in the coronal portion of threaded portion and a second groove having a helical pattern, the second groove being formed on at least a portion of the body in the apical portion of the threaded portion.

21. The dental implant of claim 20, wherein the first and the second groove both extend onto the intermediate portion of the threaded portion of the implant.

22. The dental implant of claim 9, wherein a thickness of the face of the at least one thread generally increases from the coronal portion of the threaded portion to the apical portion of the threaded portion.

23. A dental implant for supporting a dental prosthesis, the implant comprising:

a body comprising an outer surface, an apical end, a coronal end, a threaded portion and a longitudinal axis, the coronal end of the body comprising a collar, the threaded portion comprising a coronal portion, an intermediate portion and an apical portion, the threaded portion further comprising at least one thread extending from a root surface, the at least one thread comprising a coronal flank, an apical flank, and a face extending between the coronal flank and apical flank, wherein the thread face has a thickness that generally increases from the coronal portion to the apical portion and wherein at least in the apical portion the face of the at least one thread is substantially flat.

24. The dental implant of claim 23, wherein the collar of the dental implant tapers outwardly with respect to the longitudinal axis.

25. The dental implant of claim 23, comprising a first groove having a helical pattern, the first groove being formed on at least a portion of the flank of the thread and a second groove having a helical pattern, the second groove being formed on at least a portion of the body adjacent the coronal and apical flanks.

* * * * *